(12) United States Patent
Martineau et al.

(10) Patent No.: US 6,916,456 B2
(45) Date of Patent: Jul. 12, 2005

(54) PRESSURE RELIEF DEVICE FOR MEDICAL INSTRUMENT REPROCESSOR

(75) Inventors: Louis Martineau, St-Nicolas (CA); Eric Halstead, Beauport (CA)

(73) Assignee: STERIS Inc., Temecula, CA (US)

( * ) Notice: Subject to any disclaimer, the term of this patent is extended or adjusted under 35 U.S.C. 154(b) by 68 days.

(21) Appl. No.: 10/437,217

(22) Filed: May 13, 2003

(65) Prior Publication Data

US 2004/0228782 A1 Nov. 18, 2004

(51) Int. Cl.⁷ .................................................. A61L 2/00
(52) U.S. Cl. ............... 422/295; 134/169 R; 134/169 C; 137/115.01; 137/115.13; 422/296; 422/297

(58) Field of Search .................................. 422/295, 296, 422/297, 40, 33, 2; 134/169 R, 169 C; 137/115.01, 115.13

(56) References Cited

U.S. PATENT DOCUMENTS

| | | | | |
|---|---|---|---|---|
| 3,667,216 A | * | 6/1972 | De Mattia et al. | ............ 60/660 |
| 5,551,462 A | * | 9/1996 | Biermaier | ............... 134/166 C |
| 6,354,312 B1 | * | 3/2002 | Lin et al. | ................ 134/169 C |
| RE37,921 E | * | 12/2002 | Martin et al. | ................... 4/361 |

* cited by examiner

Primary Examiner—Krisanne Jastrzab
(74) Attorney, Agent, or Firm—Kusner & Jaffe; Michael A. Centanni

(57) ABSTRACT

A pressure regulating device for regulating the pressure exerted on a medical instrument in a reprocessor for microbially deactivating the medical instruments.

22 Claims, 3 Drawing Sheets

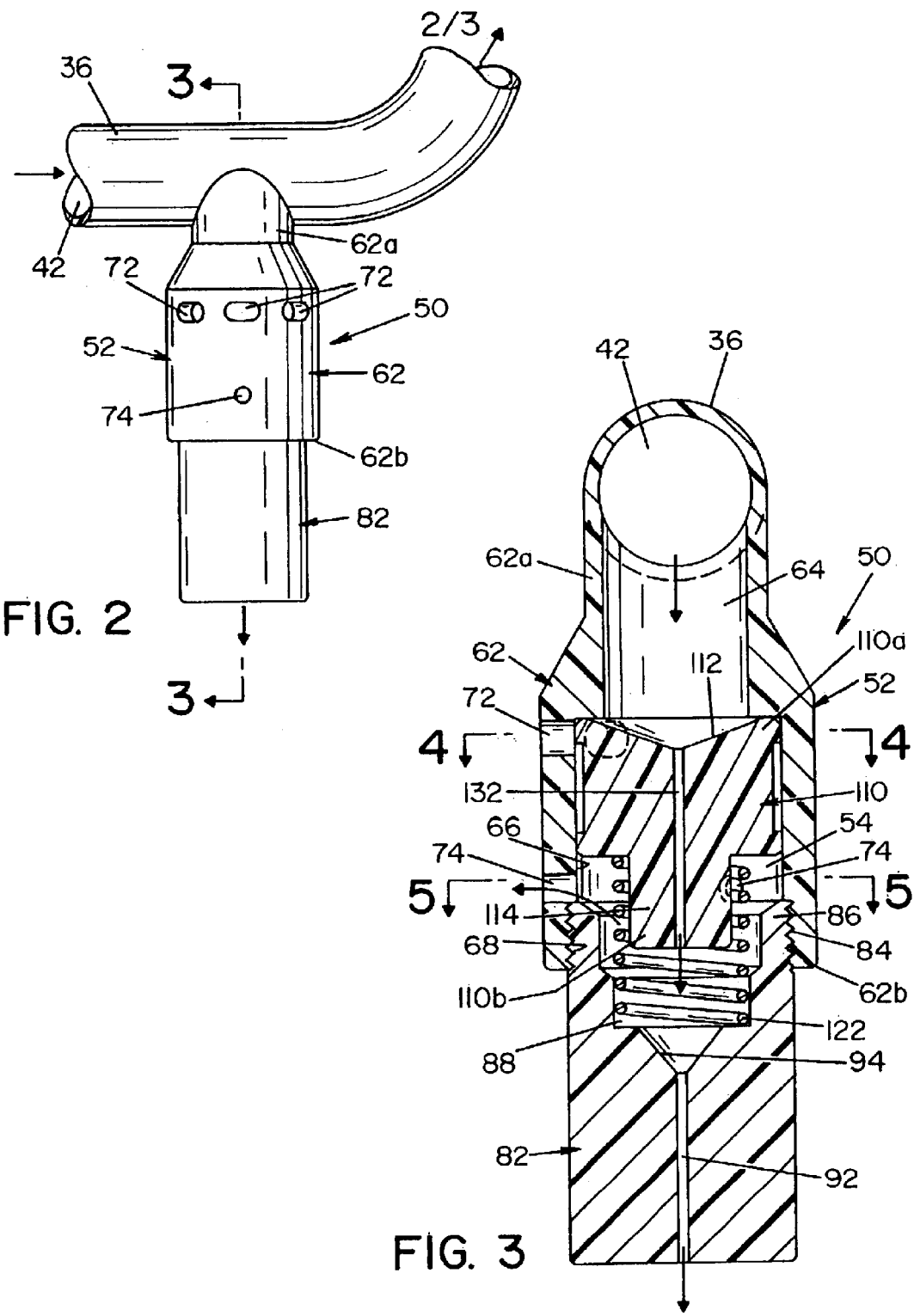

PRESSURE RELIEF DEVICE FOR MEDICAL INSTRUMENT REPROCESSOR

FIELD OF THE INVENTION

The present invention relates generally to the field of cleaning and disinfection or sterilization for microbially deactivating devices with narrow lumens, and more particularly to cleaning and disinfecting medical instruments, such as endoscopes.

BACKGROUND OF THE INVENTION

Fluid microbial deactivation systems are typically designed to cause microbes on an item to be removed or deactivated by a fluid anti-microbial agent. Such systems operate in a variety of ways, including spraying the item(s) with the anti-microbial solution, immersing an item(s) in an anti-microbial solution, surrounding the item(s) with anti-microbial vapor and the like. It has been proposed that one way to clean lumens in medical instruments is to force the anti-microbial solution through the internal lumens of the instrument. In this respect, the anti-microbial solution is supplied to the medical instrument under pressure which is sufficient to force the solution through the lumens and passageways of the medical instrument. In cleaning medical instruments in such a fashion, it is important that the pressure of the anti-microbial solution be maintained at a pressure below that which could damage delicate components within the medical instrument. Operating at pressures above the original equipment manufacturer (OEM) safe recommended levels could damage the devices. Systems that restrict flow or direct flow through narrow passages often increase the actual pressure exerted on the medical instruments.

The present invention overcomes these and other problems, and provides a pressure relief device for maintaining pressure exerted on medical instruments in a reprocessor below a safe operating level.

SUMMARY OF THE INVENTION

In accordance with a preferred embodiment of the present invention, there is provided a reprocessor for microbially deactivating medical instruments. A medical instrument is held in the reprocessor in a case that surrounds the instrument(s). The case includes fluid inlets that are operable to direct a pressurized anti-microbial solution into the case and through lumens in the instrument. A pressure regulator maintains the pressure within the case below a level that would damage the instrument. The pressure regulator includes a housing having an internal cavity. One end of the cavity is in fluid communication with the interior of the case for holding an instrument to be microbially decontaminated. A piston element is movably mounted within the internal cavity of the housing. The piston element has a first end that faces the one end of the cavity and a second end that faces another end of the cavity that is not in communication with the interior of the case. A biasing element biases the piston element toward the one end of the cavity. At least one pressure relief port is provided in the housing. The pressure relief port is in communication with the cavity and is disposed in the housing to come into fluid communication with the interior of the case when the piston element moves against the biasing element away from the one end of the cavity.

One advantage of the present invention is a device that prevents damage to sensitive medical instruments in a microbial deactivating reprocessor.

Another advantage is a device as described above that regulates the operating pressure applied to a medical instrument in a microbial deactivating system.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein:

FIG. 2 is an elevational view of a pressure relief device disposed within a fluid feed line to a case in a reprocessor, illustrating a preferred embodiment of the present invention;

FIG. 3 is an enlarged, section view taken along lines 3—3 of FIG. 2;

DETAILED DESCRIPTION OF PREFERRED EMBODIMENT

Figure 1:
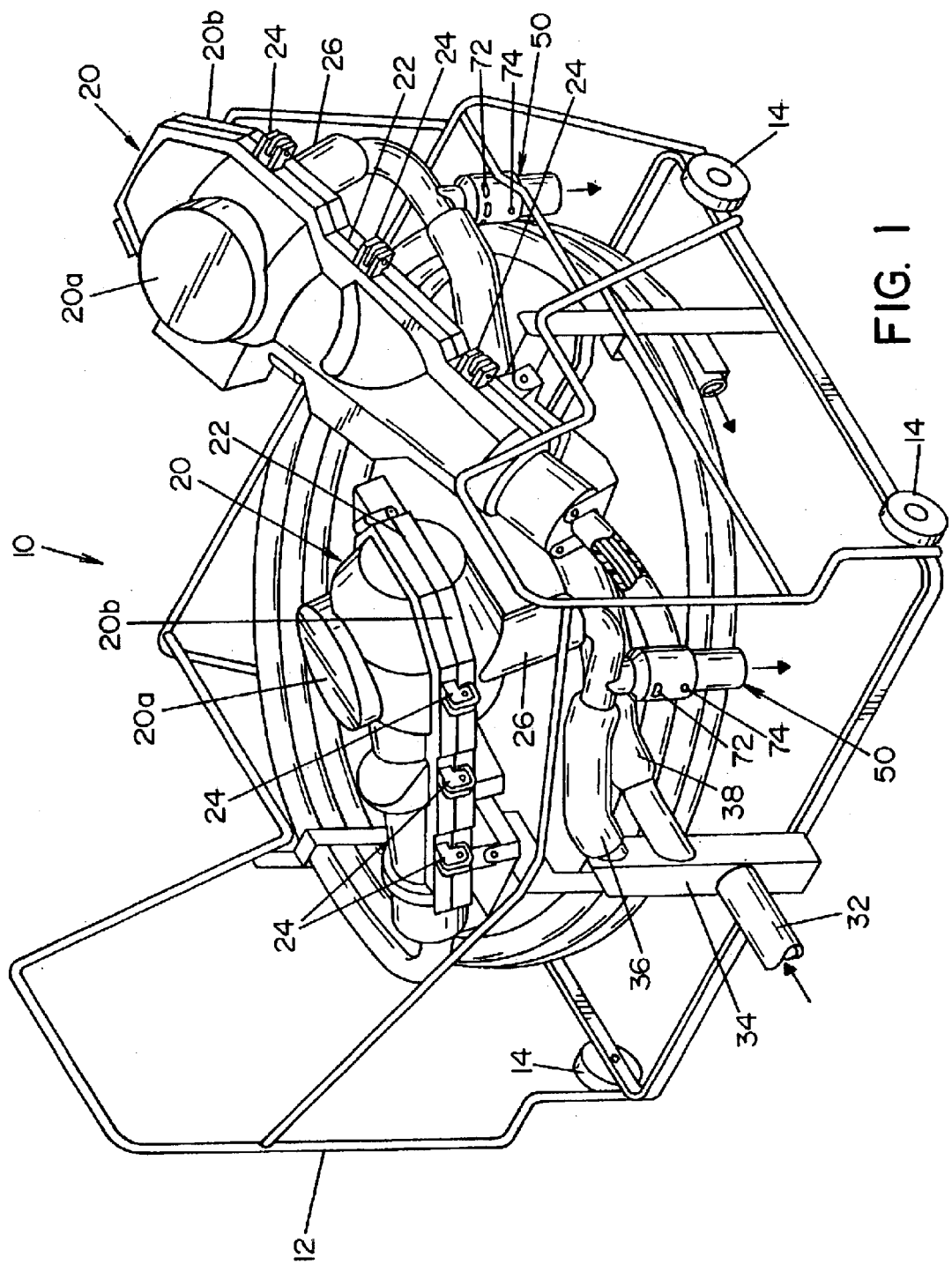
FIG. 1 is a perspective view of a rack used in a reprocessor for cleaning medical instruments, showing two cases thereon for holding medical instruments, namely an endoscope.
Figure 4:
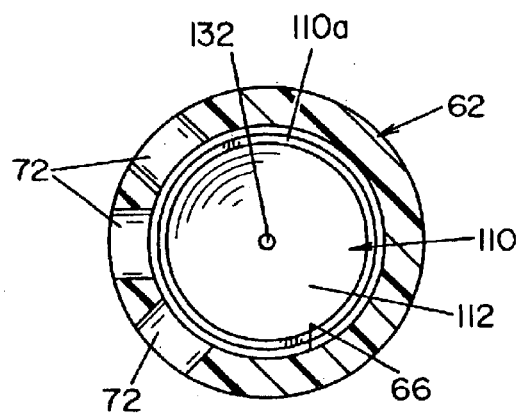
FIG. 4 is a sectional view taken along lines 4—4 of FIG. 3.
Figure 5:
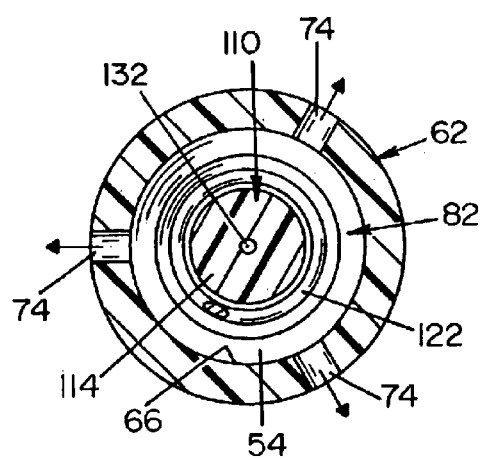
FIG. 5 is a sectional view taken along lines 5—5 of FIG. 4.

Referring now to the drawings wherein the showings are for the purpose of illustrating a preferred embodiment of the invention only, and not for the purpose of limiting same, FIG. 1 shows a rack 10 from an anti-microbial deactivation system (not shown). Rack 10 is adapted to hold medical instruments (not shown) that are to be microbially deactivated. Rack 10 is basically comprised of a tubular frame 12 having wheels 14 to allow frame 12 to move within the reprocessor. In the embodiment shown, rack 10 supports two clam-shell-like cases 20 that open and close to receive a medical instrument. In the embodiment shown, each case 20 is dimensioned to receive an endoscope (not shown). Cases 20 in and of themselves form no part of the present invention, and therefore shall not be described in great detail. Each case 20 is essentially comprised of two sections 20a, 20b that are dimensioned to separate along a parting line 22. Sections 20a, 20b have hinges 24 along one side to open and close in a clam-shell-like fashion. Cases 20 are adapted to receive endoscopes therein, and to receive an anti-microbial solution through a port 26 at the upper end thereof. The interior of each case is dimensioned such that the anti-microbial solution flows around the instrument contained therein and through the lumens of the instrument. The structure and operation of the cases are more fully described and disclosed in prior U.S. patent application Ser. No. 10/115,847, filed on 4 Apr. 2002, and entitled: AUTOMATED ENDOSCOPE REPROCESSOR, the disclosure of which is expressly incorporated herein by reference.

Cases 20 are supported within tray 10 in a predetermined orientation. Pressurized anti-microbial solution is provided to each case via a fluid feed line 32. In the embodiment shown, fluid feed line 32 is connected to a manifold 34 that splits the stream of anti-microbial solution along two paths, namely through a first branch feeder line 36 and a second branch feeder line 38. Branch feeder lines 36, 38 are connected to the upper ends of cases 20, as illustrated in FIG. 1. Each branch feeder line 36, 38 is a tubular structure that defines an internal passage 42, best seen in FIG. 3, that directs flow of the anti-microbial solution to a respective case 20. In accordance with one aspect of the present invention, a pressure relief device 50 is associated with each case 20 to regulate the pressure of the anti-microbial solution flowing therethrough. In the embodiment shown, pressure relief device 50 is attached to each branch feeder line 36, 38. It is also contemplated that pressure relief device 50 could be formed as part of, or be attached to, an instrument holding case 20.

Figure 6:
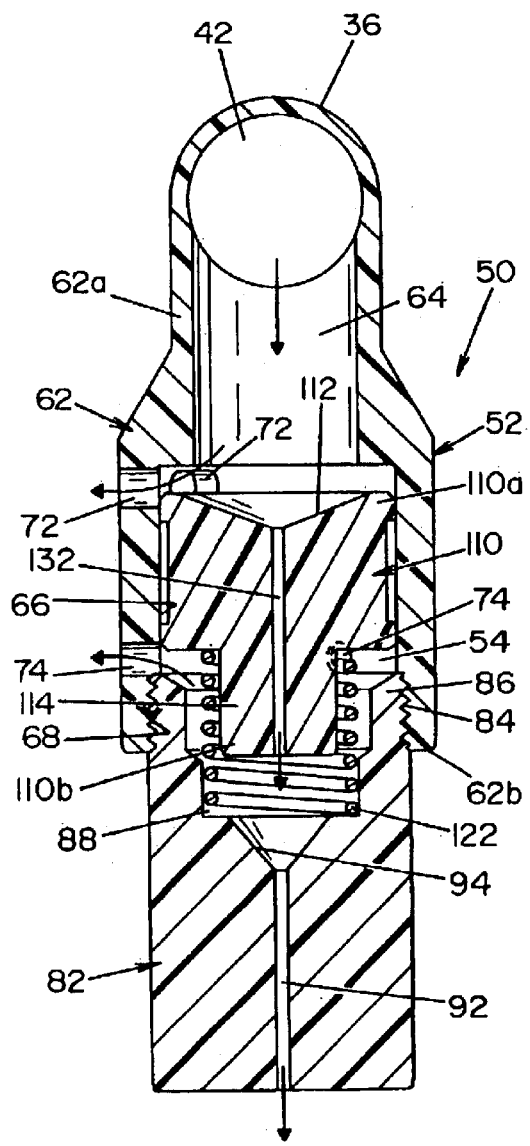
FIG. 6 is a sectional view of the pressure relief device shown in FIG. 2, showing the piston element therein moved to a pressure relief position.

Pressure relief device 50 is basically comprised of a housing 52 that defines an inner chamber or cavity 54, and a piston element 110 that is movable within cavity 54. In the embodiment shown, housing 52 is generally cylindrical in shape, and is formed to be an integral part of branch feeder line 36 or branch feeder line 38. In FIGS. 2, 3 and 6, branch feeder line 36 is shown. In the embodiment shown, housing 52 is comprised of a first housing section 62 and a second housing section 82. First housing section 62 is generally tubular in shape, and in the embodiment shown, has a first end 62a that is formed as an integral part of branch feeder line 36. First housing section 62 includes a first opening 64 that is in fluid communication with internal passage 42 through branch feeder line 36. First housing section 62 also includes a generally cylindrical cavity 66, best seen in FIG. 3. First housing section 62 has a second opened end 62b having internal screw threads 68 formed along the inner surface thereof. A plurality of pressure relief ports 72, are formed through first housing section 62 in communication with cavity 66. In the embodiment shown, three aligned, obround, pressure relief ports 72, best seen in FIG. 2, are formed through first housing section 62. A plurality of drain ports 74 are formed through first housing section 62 near opened end 62b thereof.

Second housing section 82 is generally cylindrical in shape and has external screw threads 84 formed along the outer surface of a first end 86 thereof. End 86 of second housing section 82 is dimensioned to be matingly screwed into the opened, second end 62b of first housing section 62, as shown in the drawings. End 86 of second housing section 82 also includes an inner cavity 88 that communicates with cylindrical cavity 66 of first housing section 62 to form internal housing chamber 54. Cavity 88 in second housing section 82 is generally cylindrical in shape. A drain passage 92 extends through second housing section 82 and communicates with cavity 88. A conical surface 94 connects cavity 88 in second housing section 82 to drain passage 92.

As indicated above, second housing section 82 is dimensioned to be threadingly attached to first housing section 62, and to define internal, generally cylindrical chamber 54. Chamber 54 is dimensioned to receive piston element 100 that is movable within chamber 54. Movable piston element 110 has a first end 110a with a first surface 112 that is exposed to and faces opening 64 that communicates with passage 42 in branch feeder line 36. In the embodiment shown, first surface 112 of movable piston element 110 is generally conical in shape. Piston element 110 has a second end 110b that is formed to define a generally cylindrical post 114, and that is dimensioned to be received within and move within cavity 88 in second housing section 82.

A biasing element 122 is disposed within cavity 88 of second housing section 82, and surrounds cylindrical post 114 on movable piston element 110. In the embodiment shown, biasing element 122 is in the form of a helical spring, and is operable to bias piston element 110 toward opening 64 in first housing section 62, toward passage 42 in branch feeder line 36, as shown in FIG. 3. When piston element 110 is in the position shown in FIG. 3, it obstructs, i.e., covers, pressure relief ports 72 in first housing section 62. A small passage 132 extends through piston element 110 from conical first surface 112 to second end 110b thereof.

As best seen in FIG. 3, drain ports 74 are formed in second housing section 62 at a location wherein they intersect with the area around post 114. In other words, drain ports 74 are disposed to be in communication with a low-pressure side of piston element 110, as shall be described in greater detail below.

In accordance with a preferred embodiment of the present invention, housing sections 62, 82 and piston element 110 are preferably formed of a polymeric material not affected by the reagents in the anti-microbial solution. More specifically, housing sections 62, 82 and piston element 110 are preferably formed of a polymeric material selected from the group consisting of polyolefins. In a preferred embodiment of the present invention, housing sections 62, 82 and piston element 110 are formed of polypropylene. Helical spring 122 is preferably formed of a stainless steel.

The present invention shall now be further described with respect to the operation of pressure relief device 50. During a microbial deactivation cycle of the washer, an anti-microbial solution is pumped through pressurized fluid feed line 32 through manifold 34 to the respective branch feeder lines 36, 38. The solution is then forced into cases 20 around and through the medical instruments contained therein. Biasing element 122 of pressure relief device 50 is dimensioned to maintain piston element 110 in its normal position, as shown in FIG. 3, wherein piston element 110 obstructs, i.e., covers, pressure relief ports 72 in first housing section 62. In this respect, biasing spring 122 is selected to have a force that will be overcome when the pressure within passages 42 of branch fluid feed lines 36, 38 exceed a desired, minimum pressure established for protection of the equipment within cases 20. When the pressure of the anti-microbial solution within passage 42 of either branch feeder line 36 or 38 exceeds the biasing force of spring 122, force on upper surface 112 of piston element 110 would cause piston element 110 to move downward toward second housing section 82, thereby causing the edge of piston element 110 to move past pressure relief ports 72. Depending upon the pressure exerted on piston element 110, portions or all of relief ports 72 come into fluid communication with passage 42 through the associated branch feeder line 36 or 38 to allow microbial solution to be released. The greater the pressure exerted on piston element 110, the greater the flow of the anti-microbial solution through pressure release ports 72 to release the pressure in passage 42 and ultimately to reduce the pressure exerted on the medical instrument in case 20. Anti-microbial solution released by pressure relief device 50 falls to the bottom of the washer and ultimately to a sump therein to be re-circulated through the washer system.

Some pressure within passage 42 of branch feeder line 36 will be released by some anti-microbial solution flowing through passage 132 that extends through piston element 110. Solution flowing through passage 132 enters chamber 54 below piston element 110 where it is either drained from pressure relief device 50 through drain passage 92 in second housing section 82, or is forced out of chamber 54 through drain ports 74 in first housing section 62. Drain ports 74 in first housing section 62 prevent any solution that may have collected in chamber 54 below piston element 110 from creating "back-pressure" that might interfere with the pressure regulation of piston element 110. The flow of anti-microbial solution through piston element 110 and into chamber 54 therebelow ensures full coverage of the anti-microbial solution to the interior of chamber 54 of housing 52, thus preventing any possible contamination therein.

Pressure relief device 50 is preferably oriented in a vertical direction, as shown in the drawings. In this respect, conical surface 112 on piston element 110 would cause any residual anti-microbial solution that might remain within pressure relief device 50 following a microbial deactivation cycle to be drained through fluid passage 132 in piston element 110 into cavity 54 below piston element 110. From there, conical surface 94 that communicates with drain passage 92 would allow residual fluid to be drained through and exit housing 52.

The present invention thus provides pressure relief device 50 to relieve excess operating pressure in a reprocessing system. The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. In a reprocessor for microbially deactivating medical instruments, said medical instruments being held in said reprocessor in a case that surrounds said instrument and that includes fluid inlets to direct a pressurized anti-microbial solution into said case and through lumens in said instrument, a pressure regulator for maintaining the pressure within said case below a level that would damage said instrument, said pressure regulator comprised of:
   a housing having an internal cavity, one end of said cavity being in fluid communication with the interior of a case for holding an instrument to be microbially decontaminated;
   a piston element movably mounted within said internal cavity of said housing, said piston element having a first end that faces said one end of said cavity a second end that faces another end of said cavity that is not in communication with the interior of said case and an unrestricted fluid passage extending from said first end of said piston element to said second end of said piston element; and
   a biasing element biasing said piston element toward said one end of said cavity
   at least one pressure relief port in said housing in communication with said cavity, said pressure relief port disposed in said housing to come into fluid communication with the interior of said case when said piston element moves against said biasing element away from said one end of said cavity.

2. A reprocessor as defined in claim 1, further comprising:
   a fluid opening in said housing in communication with said another end of said cavity.

3. A reprocessor as defined in claim 2, wherein said biasing element is disposed in said another end of said cavity between said piston element and said housing.

4. A reprocessor as defined in claim 3, wherein said housing is formed of two housing sections.

5. A reprocessor as defined in claim 4, wherein said housing sections are threadingly attached to each other.

6. A reprocessor as defined in claim 1, wherein said housing includes a plurality of pressure relief ports.

7. A reprocessor as defined in claim 2, further comprising a drain port in said housing, said drain port in fluid communication with the bottom of said internal cavity.

8. A reprocessor as defined in claim 1, wherein said housing is formed of a polymeric material.

9. A reprocessor as defined in claim 8, wherein said polymeric material is selected from the group consisting of polyolefins.

10. A reprocessor as defined in claim 9, wherein said polymeric material is polypropylene.

11. A reprocessor as defined in claim 1, wherein said pressure regulator is attached to a fluid line that is attached to said case.

12. In a reprocessor for microbially deactivating medical instruments, a pressure regulator for maintaining the pressure within said medical instruments below a level that would damage said instrument, said pressure regulator comprised of:
   a housing having an internal cavity, one end of said cavity being in fluid communication with an interior of an instrument to be microbially decontaminated;
   a piston element movably mounted within said internal cavity of said housing, said piston element having a first end that faces said one end of said cavity and a second end that faces another end of said cavity that is not in communication with the interior of said instrument, said first end of said piston element forming a recessed surface, said piston element having a fluid passage extending from said recessed surface of said first end of said piston element to said second end of said piston element;
   a biasing element biasing said piston element toward said one end of said cavity; and
   at least one pressure relief port in said housing in communication with said cavity, said pressure relief port disposed in said housing to come into fluid communication with the interior of said instrument when said piston element moves against said biasing element away from said one end of said cavity;
   said housing being oriented vertically such that said first end of said piston element is disposed above said second end of said piston element.

13. A reprocessor as defined in claim 12, further comprising:
   a fluid opening in said housing in communication with said another end of said cavity.

14. A reprocessor as defined in claim 13, wherein said biasing element is disposed in said another end of said cavity between said piston element and said housing.

15. A reprocessor as defined in claim 14, wherein said housing is formed of two housing sections.

16. A reprocessor as defined in claim 15, wherein said housing sections are threadingly attached to each other.

17. A reprocessor as defined in claim 12, wherein said housing includes a plurality of pressure relief ports.

18. A reprocessor as defined in claim 13, further comprising a drain port in said housing, said drain port in fluid communication with the bottom of said internal cavity.

19. A reprocessor as defined in claim 12, wherein said housing is formed of a polymeric material.

20. A reprocessor as defined in claim 19, wherein said polymeric material is selected from the group consisting of polyolefins.

21. A reprocessor as defined in claim 20, wherein said polymeric material is polypropylene.

22. A reprocessor as defined in claim 12, wherein said pressure regulator is attached to a fluid line that is fluidly connected to a passageway within said instrument.

* * * * *